United States Patent
Wuthrich

(10) Patent No.: US 6,647,290 B2
(45) Date of Patent: Nov. 11, 2003

(54) CHARGE-BASED DEFIBRILLATION METHOD AND APPARATUS

(75) Inventor: Scott A. Wuthrich, Reading, MA (US)

(73) Assignee: Koninklijke Philips Electronics N.V., Eindhoven (NL)

(*) Notice: Subject to any disclaimer, the term of this patent is extended or adjusted under 35 U.S.C. 154(b) by 0 days.

(21) Appl. No.: 09/484,983

(22) Filed: Jan. 18, 2000

(65) Prior Publication Data

US 2003/0074025 A1 Apr. 17, 2003

(51) Int. Cl.⁷ .................................. A61N 1/39
(52) U.S. Cl. .................................. 607/5; 607/8
(58) Field of Search ...................... 607/7, 8, 5

(56) References Cited

U.S. PATENT DOCUMENTS

| | | | | |
|---|---|---|---|---|
| 5,243,975 A | * | 9/1993 | Alferness et al. | 607/7 |
| 5,540,724 A | * | 7/1996 | Cox | 607/8 |
| 5,749,904 A | * | 5/1998 | Gliner et al. | 607/7 |
| 5,800,462 A | * | 9/1998 | Lopin et al. | 607/7 |
| 5,944,742 A | * | 8/1999 | Brewer et al. | 607/6 |
| 6,208,896 B1 | * | 3/2001 | Mulhauser | 607/5 |
| 6,208,898 B1 | * | 3/2001 | Gliner et al. | 607/8 |

* cited by examiner

Primary Examiner—George R. Evanisko
Assistant Examiner—Roderick Bradford

(57) ABSTRACT

A defibrillation method and apparatus are described for delivering a desired quantity of electric charge to a patient. The method and apparatus are applicable both to external defibrillation and to defibrillation by an implanted device. The method includes determining one or more intended waveform parameters based on the desired quantity of electric charge and, optionally, on one or more patient impedance values. A defibrillation waveform is then generated and applied to the patient based on the intended waveform parameters. The patient impedance values may be predetermined or operator-selected, or the method may include the step of determining the patient impedance values. Patient impedance values may be determined prior to, substantially contemporaneous with, and/or during application of the defibrillation waveform to the patient. If a patient impedance value is determined to have changed from a previously determined value, then the intended waveform parameters may be adjusted based on this change in order to provide that the desired quantity of charge is applied to the patient.

16 Claims, 8 Drawing Sheets

CHARGE-BASED DEFIBRILLATION METHOD AND APPARATUS

BACKGROUND OF THE INVENTION

1. Field of the Invention

The present invention relates generally to a defibrillator and, more particularly, to defibrillators that provide variable waveforms.

2. Related Art

An external defibrillator is a device used to administer a high intensity electrical shock through two or more electrodes, commonly referred to as "paddles" or "pads," to the chest of a patient in cardiac arrest. Energy typically is stored in a charge-storage device (e.g., a capacitor) and is then electrically discharged into the patient through the electrode circuit.

If an initial attempt at defibrillation is not successful, one or more additional attempts typically are made. However, repeated defibrillation attempts, particularly if they are made at increasing levels of intensity, are increasingly likely to cause damage to the heart or other body tissue. Although the threshold levels for damage are not well quantified, it appears that there is not a great deal of margin between an effective defibrillation level and a damaging defibrillation level. Also, the delay associated with repeating the defibrillation procedure may allow the patient's condition to deteriorate. For example, metabolic imbalance and hypoxia may develop in response to prior attempted resuscitations. Moreover, the development of these conditions typically makes it more difficult to defibrillate the patient and, even if defibrillation is achieved, reduces the prospect of successful recovery. Thus, early and optimal selection of various waveform parameters is crucial to improving the chances of a successful outcome.

One set of waveform parameters thought to be important in determining the safety and success of the defibrillation procedure are those that define the shape of the defibrillation waveform. Waveforms having a variety of shapes have conventionally been used. Some defibrillators employ monophasic (single polarity) voltage pulses. Others employ biphasic (both positive and negative polarity) pulses. Monophasic or biphasic pulses may be damped-sinusoidal, truncated-exponential, constant "tilt" (a measure of the difference between the start and end voltage, often expressed as the difference between the initial and final voltages, divided by the initial voltage), combinations of such forms, and so on. Many other forms, such as rectilinear pulses, are possible. In addition, the shape of a waveform may be adjusted by varying its amplitude or duration, or the amplitudes or durations of one or more of its constituent parts. Some conventional approaches for determining what are considered to be optimal shapes for defibrillation waveforms, delivered by both implanted and external defibrillators, are described in U.S. Pat. No. 5,431,686 to Kroll et al., U.S. Pat. No. 4,953,551 to Mehra et al., and U.S. Pat. No. 4,800,883 to Winstrom.

The choice of waveform shape also may depend on whether the defibrillator is implanted or is external. If the defibrillator is implanted, the patient's unique electrical characteristics and overall physiology may be investigated and the waveform tailored to that particular patient's needs. External defibrillators, in contrast, are intended to be applied to numbers of patients that have generally varying physiological characteristics. Moreover, a patient may require different waveforms for optimal operation depending, for example, on the contact that is achieved between the electrode and the patient. Thus, external defibrillators may be designed for optimal use on an average patient. Alternatively, they may be designed so that they are capable of providing a variety of waveforms depending on an evaluation of the patient's physiology, the electrical connection achieved between the electrode and the patient, new knowledge about the operation and affect of electrotherapeutic discharges, or other factors.

Several factors have been used to determine the defibrillation waveform parameters. In particular, many defibrillators presently in use are designed to deliver one or more specific quantities of energy, typically measured in joules, to the patient's heart. With respect to external defibrillators, practical considerations have contributed to an emphasis on energy-based defibrillation methods. In particular, energy is a relatively easy quantity to control at the power levels and pulse width's required for transthoracic defibrillation.

Guidelines of the American Heart Association applicable to external defibrillation suggest that a first discharge be administered to deliver a total energy of 200 joules to the patient, a second discharge be administered to deliver 200 to 300 joules, and a third discharge be administered to deliver 360 joules. In conformance with these guidelines, many conventional external defibrillators are designed to deliver these quantities of energy to a patient assuming a typical transthoracic impedance (e.g., 50 ohms). Other defibrillators take into account the variability of transthoracic impedance from one patient to another. In general, these defibrillators measure the transthoracic impedance of the patient and adjust the amount of energy stored in a discharge capacitor or other energy storage device in order to achieve a desired amount of energy applied to the patient's heart. Some of these conventional defibrillators also vary the shape of the defibrillation waveform as a function of transthoracic impedance and the quantity of energy to be delivered. The rationales for these and other conventional energy-based approaches are described in numerous sources such as U.S. Pat. No. 4,771,781 to Lerman, U.S. Pat. No. 5,620,470 to Gliner, et al., U.S. Pat. No. 5,607,454 to Cameron, et al., and International Application PCT/US98/07669 (PCT International Publication No. WO 98/47563).

The Lerman patent also describes another type of conventional design in which the defibrillation discharge is determined based on current delivered to the patient. In particular, Lerman describes a method for calculating a level of energy necessary to deliver to the patient an amount of peak current pre-selected by an operator. A measured transthoracic resistance of the patient, together with the selected peak defibrillation current, are used to control the charge that is applied to a discharge capacitor of the defibrillator. Upon discharge, the selected level of peak current is applied to the patient. U.S. Pat. No. 4,840,177 to Charbonnier, et al., also describes a method for determining a charge level for an energy storage device such that, when the device is discharged, a desired current flows into the patient. These and other conventional current-based designs seek, among other things, to limit or avoid the damage that may be inflicted by the delivery of an excessive amount of energy. For example, in situations in which the transthoracic resistance is low, a particular selection of energy for discharge into the patient will result in a larger applied current than would be realized if the transthoracic resistance had been high. On the theory that it is the application of current, rather than energy per se, that achieves the desired defibrillation, the energy discharged into a low-resistance patient therefore may be selected to be less than it would be for a high-resistance patient. Thus, the supposed therapeutic benefit is achieved while exposing the patient to a level of energy that is thought to be less likely to cause damage. Various other conventional techniques for determining defibrillation discharge parameters based on operational parameters such as desired energy, current, and/or shape are noted and discussed in the above noted PCT Publication No. 98/47563.

SUMMARY OF THE INVENTION

Although current-based defibrillators are feasible, they typically must operate over a wide range of energy and power in order to deliver a specified current over a wide range of possible transthoracic impedances. These requirements often complicate the design of conventional current-based defibrillators. Moreover, it is not clear that the delivery of current, per se, is the mechanism that achieves defibrillation. (See Charbonnier, "External Defibrillators and Emergency External Pacemakers," *Proceedings of the IEEE*, vol. 84, number 3, pages 487–499, particularly at pages 491–93.) Up to a certain point, a longer current pulse requires less peak current to be effective. Thus, the inventor has concluded that defibrillation may be achieved as a result of the accumulation of charge (current over time) rather than by the current per se. Further support for this view may be deduced from what is known of the defibrillation mechanism at the cellular level. The cell walls of heart muscle tissue, like other cells in the human body, have a capacitance. Defibrillation is thought to be accomplished by cell depolarization and introduction of a refractory period. (See Jones, et al., "Cellular Excitation with High-Frequency Chopped Defibrillator Waveforms," *Proceedings of the 16th Annual International Conference of the IEEE Engineering in Medicine and Biology Society,* (IEEE, 1994), pages 17–18.). The inventor concludes that defibrillation may be accomplished by producing a voltage potential difference across the cell wall, and that this voltage potential difference depends on the amount of charge provided rather than on the current or energy levels applied, per se.

Accordingly, in one aspect of the present invention, a method for delivering a desired quantity of electric charge to a patient is disclosed. The term "desired" in this context means that it is an objective of the apparatus or method of the invention to deliver to the patient a particular quantity, or dosage, of electric charge.

In some embodiments of the method, the desired charge is predetermined. The term "predetermined" in this context means that, in some implementations of the present invention, the operator of the defibrillator does not select a desired charge. Rather, a default value of electric charge is assumed to be the desired value. As described below in accordance with an illustrated embodiment, this default value may be stored in a memory location accessible by a microprocessor that determines the duration, amplitude, form, and other waveform parameters such that the desired value of electric charge is delivered to the patient's heart. The default value may also be stored in firmware or determined by configurations and/or values of hardware components.

In some cases, the operator may desire to deliver a quantity of charge different than a predetermined, or default, value. In these cases, the desired quantity of electric charge is referred to herein as being "operator-selected." Some reasons that the operator may desire to select a quantity of electric charge include that application of a default value has not achieved the desired therapeutic effect, that new research or experience indicates that the default value is no longer the best choice in general, that new research or experience indicates that the default value is no longer the best choice in view of certain characteristics of the patient (e.g., weight), and so on. It is not precluded that a default value may be changed due, for example, to new research or experience. In such cases, the default value may be reprogrammed in accordance with known techniques such as by changing values in software or firmware, or by changing hardware components.

The method includes the step of determining intended waveform parameters based at least in part on a desired quantity of electric charge. The intended waveform parameters may also be based at least in part on one or more patient impedances. Waveform parameters may include the form, duration, or amplitude of a waveform. As described in greater detail below, these waveform parameters may be determined in various ways. The word "determined" in this context may mean that the parameters are calculated (such as, for example, computing the necessary amplitude and/or duration of a rectilinear voltage pulse such that a desired quantity of current over time, i.e., charge, will be delivered to a patient of a certain impedance). Also, "determined" may refer to the application of any of a variety of other known techniques that may be employed to select, retrieve, or in any other way identify waveform parameters that would provide the desired charge if a waveform having these parameters were applied to a patient with a certain impedance. Some examples of other techniques, described in greater detail below, include using a look-up table, or search and compare techniques, to find templates of appropriate model waveforms as stored, for example, in computer memory.

The method also includes the step of generating an applied defibrillation waveform based on the intended waveform parameters. That is, a waveform is generated for application to the patient in accordance with the intended waveform parameters. However, in some implementations, these two functions could be combined into a single function in which the determining and generating of a defibrillation waveform are combined. For example, an operator could employ an electromechanical switch that selects one of two charged capacitors (or selects one of two voltages to which a single capacitor is charged) and discharges the selected capacitor (or selected voltage) into the patient. In this simplified example, the "determining" of the intended waveform is accomplished by selecting the capacitor (which may be predetermined to provide one of two desired quantities of charge into a patient of an assumed impedance) and the "generating" of the waveform is accomplished by enabling the selected capacitor to discharge into the patient. In an even simpler example, one capacitor or voltage could be used based on a predetermined (e.g., pre-calculated) voltage that will provide a desired quantity of charge to a patient of an assumed impedance.

In some implementations, a further step in the method is that of electrically coupling the applied defibrillation waveform to the patient. This step typically may be accomplished by an operator applying the electrode to the patient. Also, when the electrodes have already been applied to the patient, this step may be accomplished when the operator activates an activator that, among other things, closes a patient isolation relay so that an electrical circuit from the defibrillator to the patient is completed.

A patient may be assumed to have, or may be determined to have, more than one impedance value. This situation may occur for several reasons. For example, a patient impedance value may be assumed or estimated in advance (i.e., predetermined) based, for instance, on average patient impedance values. Also, an operator may select a patient impedance value from one of two or more predetermined values. In the case of an external defibrillator, the estimation or selection of these values may reflect various assumptions regarding a typical value of transthoracic impedance. For instance, the value may be selected to be 50 ohms, 80 ohms, or another value that may be thought to more accurately represent the physiology of a patient population. Another reason that there may be more than one patient impedance value is that, in the case of an external defibrillator, the electrical characteristics of the connection between the electrode and the patient may change during the time that the defibrillation waveform is applied, or from one application to another. This change may result, for example, from variations in pressure or placement of the paddles. Also, the patient's physiology may be altered by the application of the defibrillation discharge or for other reasons.

Yet another reason for variations in patient impedance value is the difference circumstances applicable to external and implanted defibrillators. As is evident, a transthoracic patient impedance value will be different than a patient impedance value presented to an implanted defibrillator in which the defibrillation waveform is applied directly to the heart. Thus, in implementations of the method involving external defibrillation, the patient impedance is a transthoracic impedance and, in implementations involving internal defibrillation, the patient impedance is a heart impedance.

In addition, variations in patient impedance values may result from measurements of a particular patient's impedance at one or more times. Thus, in some aspects, the invention is a method that also includes the step of determining at least one of the patient impedance values. This determination may be made in various ways. In accordance with one technique, a value is sensed that is indicative of an impedance of the patient prior to the electrical coupling of the applied defibrillation waveform to the patient. In accordance with another technique, a value is sensed that is indicative of an impedance of the patient substantially contemporaneous with starting the electrical coupling of the applied defibrillation waveform to the patient. This technique also includes determining an adjustment, if any, to the intended waveform parameters based on the sensed value. The purpose of this adjustment is to apply the desired quantity of charge to the patient. Thus, the applied defibrillator waveform is adjusted based on this determination.

The method may also include the steps of sensing one or more values indicative of one or more impedances of the patient during electrical coupling of the applied defibrillation waveform to the patient and determining an adjustment, if any, to the intended waveform parameters based at least in part on the sensed one or more values. The applied defibrillation waveform is adjusted based on this determination. There may be a number of these adjustments made during the application of the defibrillation waveform. For example, it may be sensed shortly after initiation of the defibrillation discharge into the patient that the patient's impedance has changed from an initial sensed value. The applied defibrillation waveform is adjusted accordingly. Subsequently, during the same defibrillation discharge, it may be sensed that the patient's impedance has again changed, and thus the applied defibrillation waveform is again adjusted. As noted, these adjustments are made so that the desired quantity of charge is applied to the patient notwithstanding the changes in the patient's impedance.

In some aspects, the invention is a method that includes comparing the intended waveform parameters with the applied waveform parameters of the applied defibrillation waveform during electrical coupling of the applied defibrillation waveform to the patient. When a difference between the intended and actual waveform parameters reaches a threshold value, the method includes adjusting the applied waveform parameters of the applied defibrillator waveform to conform with the intended waveform parameters. Also, in some aspects, the determination of intended waveform parameters may include determination of any of the following parameters: form, phase, timing of phase transition, maximum duration, minimum duration, maximum voltage, minimum voltage, maximum current, minimum current, maximum energy, minimum energy, maximum power, and minimum power. It will be understood that these intended waveform parameters are illustrative only, and that any other parameter for describing, specifying, modeling, or otherwise representing a waveform may be employed as a waveform parameter in accordance with the invention.

The applied defibrillation waveform in various aspects of the invention includes a set of voltage values. This waveform may include, for example, a monophasic voltage pulse, a biphasic voltage pulse, etc. The applied defibrillation waveform in various aspects of the invention may also include a set of current values.

In other aspects, the invention includes a method for delivering a desired quantity of electric charge to a patient. The desired quantity of electric charge may be predetermined, or it may be operator-selected. This method includes the steps of providing a flow of current over time through an electrical coupling to the patient, and stopping the current flow when a desired quantity of electric charge has been delivered. In some implementations, the step of providing a flow of current over time includes determining intended waveform parameters of the current waveform. This determination may be based on any one or more of the following illustrative and non-exclusive parameters: one or more patient impedance values, the desired quantity of electric charge, shape, phase, timing of phase transition, maximum duration, minimum duration, maximum voltage, minimum voltage, maximum current, minimum current, maximum energy, minimum energy, maximum power, and minimum power.

The present invention in some aspects is a method for delivering a desired quantity of electric charge to a patient. The method includes the steps of determining an impedance of the patient; determining a charge voltage of an energy-storage device based on the impedance and on the desired quantity of electric charge to be delivered to the patient; charging the energy-storage device to the charge voltage; and providing the charged voltage to electrodes in response to a discharge request. This method may also include determining a flow of delivered current into the patient due to discharging the charged voltage. In addition, the steps may be included of determining, based on the flow of delivered current over time, a delivered quantity of electric charge delivered to the patient; continuing discharging the charged voltage into the patient until the delivered quantity of electric charge is equal to the desired quantity of electric charge.

In yet further aspects, the present invention is a defibrillator for delivering a desired quantity of electric charge from an energy storage device to a patient. The defibrillator includes a charge-delivery processor that determines a charge voltage of the energy-storage device based on at least one patient impedance and on delivering the desired quantity of electric charge to be delivered to the patient. The defibrillator also has an applied waveform generator that charges the energy-storage device to the charge voltage determined by the charge-delivery processor. The defibrillator may further include at least one sensor for determining a patient impedance. The applied waveform generator may also discharge the charged voltage into a patient in response to a discharge command. Also, the defibrillator may include a feedback processor that determines, during the discharge of the charged voltage into the patient, an instantaneous quantity of current delivered to the patient due to discharging the charged voltage. In this aspect of the invention, the charge-delivery processor further determines, based on the flow of delivered current over time, a delivered quantity of electric charge delivered to the patient, and determines when the delivered quantity of electric charge is substantially equal to the desired quantity of electric charge. Also in this aspect of the invention, the applied waveform terminates the discharge of the charged voltage into the patient responsive to the charge-delivery processor determining that the delivered quantity of electric charge is substantially equal to the desired quantity of electric charge.

The charge-delivery processor may also determine one or more intended waveform parameters selected from the following illustrative and non-limiting waveform parameters: form, phase, timing of phase transition, maximum duration, minimum duration, maximum voltage, minimum voltage, maximum current, minimum current, maximum energy, minimum energy, maximum power, and minimum power. Also, the applied waveform generator determines the discharge of the charged voltage into the patient responsive to the one or more intended waveform parameters.

In yet another aspect of the invention, a defibrillator is disclosed for delivering a desired quantity of electric charge to a patient. The defibrillator includes a charge-delivery processor that determines one or more intended waveform parameters based at least in part on the desired quantity of electric charge. The defibrillator may also have an applied waveform generator that generates an applied defibrillation waveform based on one or more of the intended waveform parameters.

In a still further aspect of the invention, a defibrillator for delivering a desired quantity of electric charge to a patient is also disclosed. The defibrillator includes a charge-determined waveform that provides a flow of current over time through an electrical coupling to the patient and stops the flow of current when the flow of current over time indicates that the desired quantity of electric charge.

The above aspects and implementations of the invention are not necessarily inclusive or exclusive of each other and may be combined in any manner that is non-conflicting and otherwise possible, whether they be presented in association with a same, or a different, aspect or implementation of the invention. The description of one aspect is not intended to be limiting with respect to other aspects. Also, any one or more function, step, operation, or technique described elsewhere in this specification may, in alternative aspects, be combined with any one or more function, step, operation, or technique described in the summary. Thus, the above aspects are illustrative rather than limiting.

BRIEF DESCRIPTION OF THE DRAWINGS

The above and further advantages of the invention will be more clearly appreciated from the following detailed description when taken in conjunction with the accompanying drawings, in which like reference numerals indicate like structures or method steps in which the leftmost digit of a reference numeral indicates the number of the figure in which the referenced element or step first appears (for example, the element 210 appears first in FIG. 2), and wherein.

DETAILED DESCRIPTION

The attributes of the present invention and its underlying method and architecture will now be described in greater detail with reference to an illustrative defibrillator, referred to as defibrillator 105. For illustrative purposes, defibrillator 105 generally will be assumed to be an external defibrillator. However, the invention is not limited to this illustrative example. For example, the invention may be implemented in an implanted defibrillator or other electrotherapy device.

Figure 1:
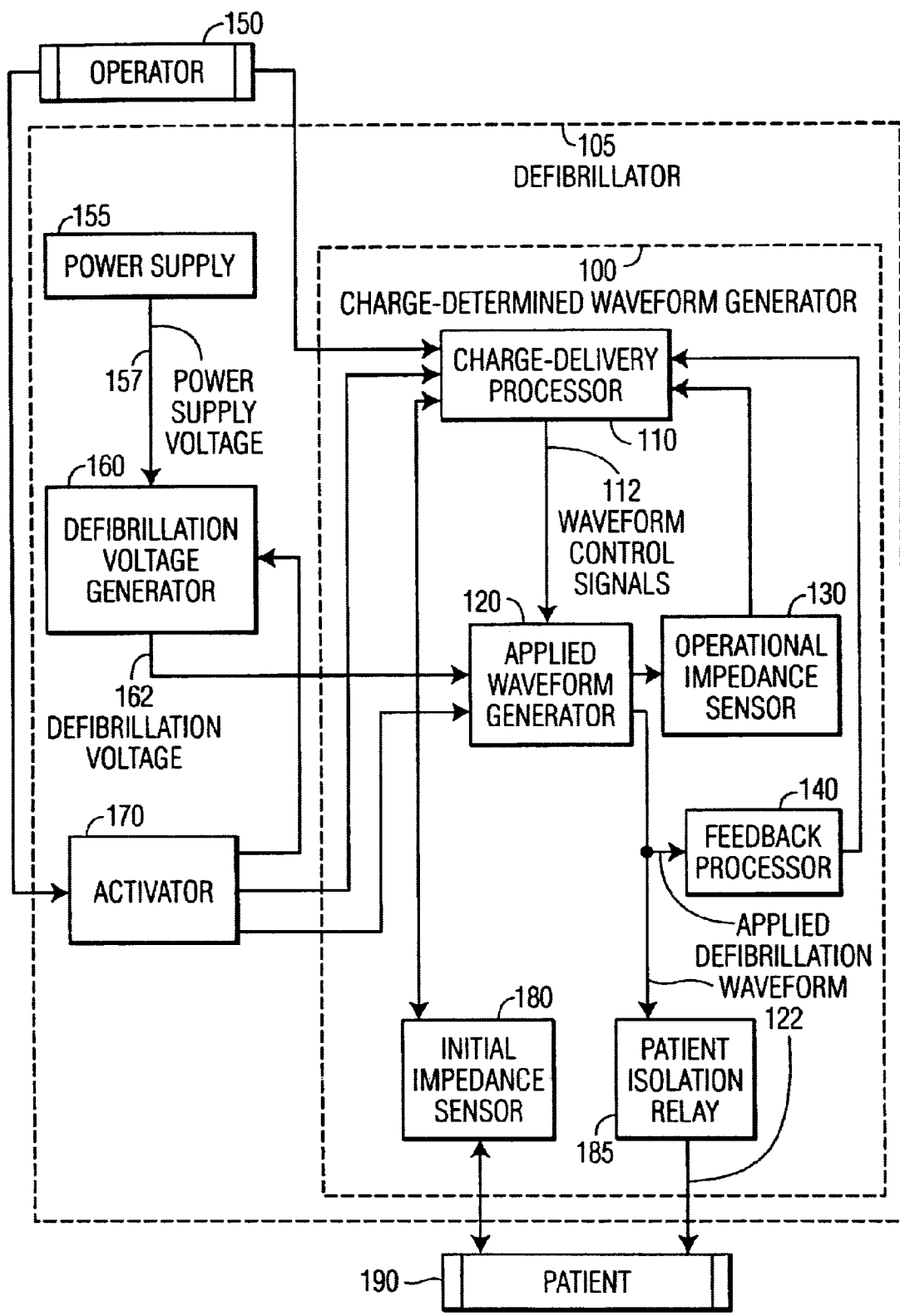
FIG. 1 is a functional block diagram of one embodiment of a defibrillator, including a charge-determined waveform generator, in accordance with the present invention.

FIG. 1 is a functional block diagram of defibrillator 105. As shown in FIG. 1, defibrillator 105 includes power supply 155, defibrillation voltage generator 160, and activator 170, all of which are known elements of a defibrillator. In accordance with the present invention, defibrillator 105 also includes a charge-determined waveform generator 100.

Power supply 155 may be any of a variety of known power supplies appropriate for use with external or internal defibrillators. Power supply 155 provides a power supply voltage 157 that is processed in accordance with known techniques by defibrillation voltage generator 160 to generate defibrillation voltage 162. Defibrillation voltage 162 is provided to component of charge-determined waveform generator 100 as described below. Defibrillation voltage generator 160 is activated by activator 170. Because of the high energy levels generated by generator 160, and the dangers to patients or operators due to an accidental discharge of defibrillator 105, generator 160 typically remains in a deactivated state until its use is required to defibrillate a patient. Activator 170 is, in turn, enabled by operator 150. In an external defibrillator, operator 150 typically is a human being, but it may be a machine. In an internal defibrillator, operator 150 typically is a device that detects ventricular fibrillation, or other abnormal heart activity that may be susceptible to electrotherapy, and automatically activates the internal defibrillator by enabling activator 170. Activator 170 may be any of a variety of known devices, typically including known switches, relays, logic circuits and elements, and/or other elements. In the illustrative embodiment activator 170 activates components of charge-determined waveform generator 100, as described below.

Charge-Determined Waveform Generator 100

Charge-determined waveform generator 100 generates an applied defibrillation waveform 122 that is applied to a patient 190. The term "charge-determined" means that waveform 122 is determined so that a desired quantity of electric charge is applied to the patient's heart. In FIG. 1, applied defibrillation waveform 122 is applied to patient 190 through a patient isolation relay 185, described below, and electrodes (not shown) applied to the chest of patient 190.

In the illustrated embodiment as shown in FIG. 1, the two principal functions of charge-determined waveform generator 100 are represented by charge-delivery processor 110 and applied waveform generator 120. Charge-delivery processor 110 generates waveform control signals 112 based at least in part on one or more patient impedance values and the quantity of electric charge that is desired to be applied to the patient. Under the control of control signals 112, applied waveform generator 120 then generates applied defibrillation waveform 122 that applies the desired quantity of electric charge to the patient. Other functional elements of charge-determined waveform generator 100 include operational impedance sensor 130, feedback processor 140, and initial impedance sensor 180, which are known elements of a defibrillator. They are described below in connection with the operation of applied waveform generator 120, after charge-delivery processor 110 is more fully described.

Charge-Delivery Processor 110

Figure 2:
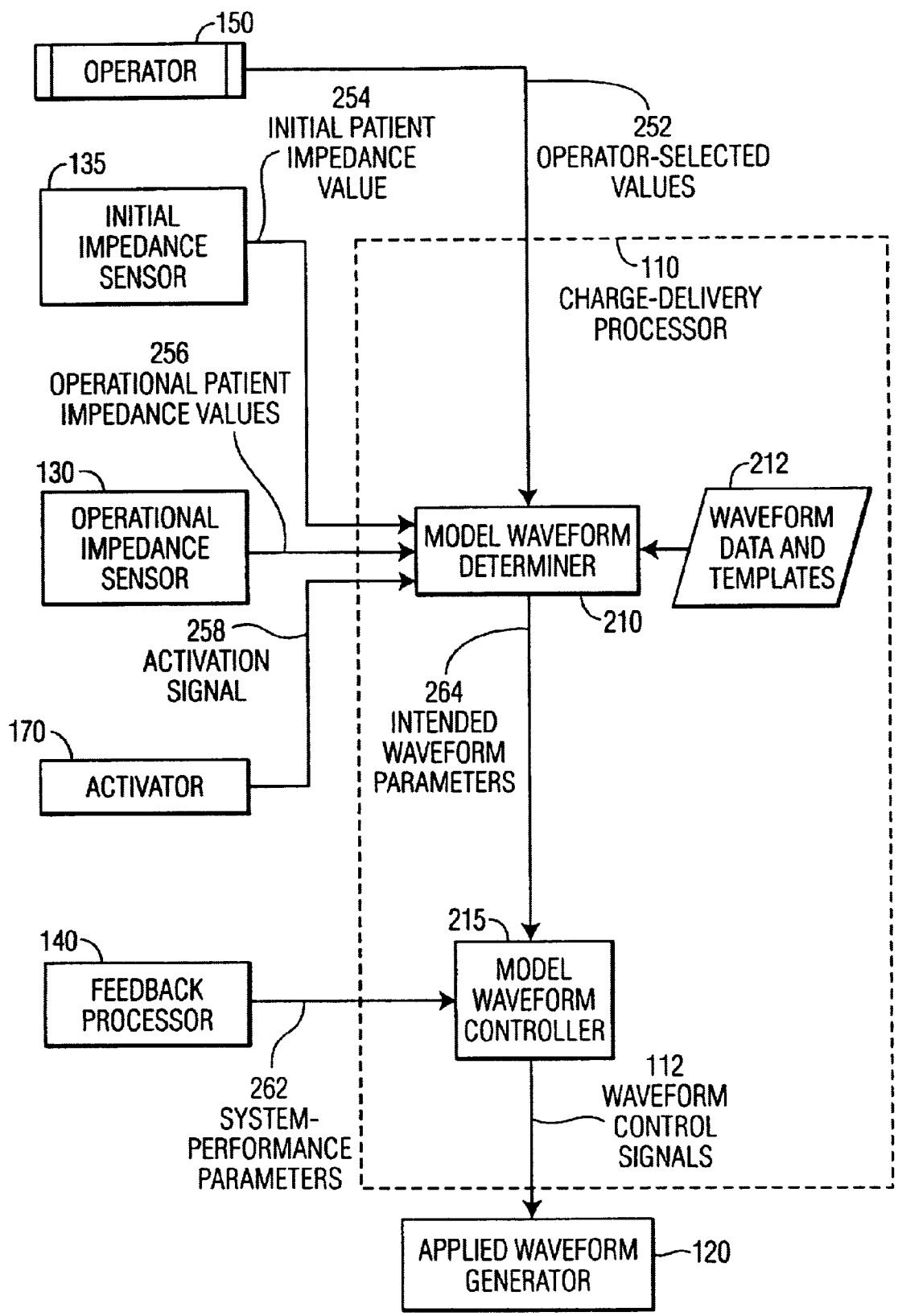
FIG. 2 is a functional block diagram of one embodiment of a charge-delivery processor of the charge-determined waveform generator of FIG. 1.

FIG. 2 is a functional block diagram of charge-delivery processor 110. As noted, charge-delivery processor 110 generates waveform control signals 112 based on a number of factors, some of which may be desired waveform parameters. In the illustrated embodiment disclosed herein, the factors include one or more patient impedance values and the quantity of electric charge that is desired to be delivered to the patient. Charge-delivery processor 110 includes model waveform determiner 210 that determines intended waveform parameters 264 based on these factors, and model waveform controller 215 that, based on intended waveform parameters 264, issues waveform control signals 112 to applied waveform generator 120.

The functions of determiner 210 and controller 215 may be implemented by any of a variety of known or future microprocessors, or similar known or future devices, controlled by software stored in memory units of, or associated with, those microprocessors or devices or by programs executed under the control of firmware, hardware, or any combination thereof. For example, the functions of determiner 210 and controller 215 may be implemented by an Intel 80196 microprocessor with associated ROM. It will be understood that the functions performed by determiner 210 and controller 215 may be described as being performed by a single functional element, e.g., by a single microprocessor with associated memory. The functions of charge-delivery processor 110 are described as being carried out by two functional elements (210 and 215) for convenience and clarity of illustration only.

As noted, the factors used by determiner 210 to determine intended waveform parameters 264 may include: a desired quantity of electrical charge to be applied to the patient's heart, one or more values representing the patient's impedance, and a waveform shape including amplitude and duration. Some or all of these factors may be specified by operator 150, as represented in FIG. 2 by operator-selected values 252. Also, some or all of these factors may be predetermined, as represented by waveform data and templates 212. This predetermined information may be stored in registers of a microprocessor, in ROM, in another memory storage device accessible by the microprocessor, in specialized electrical circuits, or in accordance with any other known or future technique for storing data. Furthermore, the patient impedance value may also be measured, such as by initial impedance sensor 135 or operational impedance sensor 130. These measured values are represented, respectively, by initial patient impedance value 254 and operational patient impedance value 256. Each of these possible sources of information are now described in greater detail.

Operator-selected values 252 may be selected by operator 150 using any of a variety of known techniques. For example, as noted, operator 150 may manipulate switches, dials, or other electromechanical devices to select certain values; provide values using an input device such as a graphical user interface with a display device (not shown); use a combination of these techniques; and so on. Using known techniques, operator-selected values 252 may be stored in registers of a microprocessor, in ROM, or in another memory storage device accessible by the microprocessor. These stored values are then used by the illustrative microprocessor of determiner 210 to determine intended waveform parameters 264, as described below.

In some cases, operator-selected values 252 may completely determine intended waveform parameters 264. In these cases, the function of model waveform determiner 210 is simply that of passing on to model waveform controller 215 the values selected by operator 150. For example, operator 150 may specify that it is desired to apply a charge of 0.15 coulombs to a patient having an assumed impedance represented by a resistance of 50 ohms, using a rectilinear voltage pulse having an amplitude of 750 volts and a duration of 10 milliseconds. (0.15 coulombs=750 volts/50 ohms×10 milliseconds.) These selections completely describe a voltage waveform for applying the desired quantity of charge to the patient. Thus, no calculations or other determinations need be made by model waveform determiner 210. In other examples, operator 150 may select different amplitudes or duration, or may select a sinusoidal waveform, and so on, such that the charge delivered to the patient (calculated or otherwise determined by operator 150 based on the amount of current provided over time) is substantially equal to the desired quantity of charge.

More generally, however, operator 150 specifies fewer than all of the values of the previous examples. For example, operator 150 may specify simply that it is desired to apply a charge of 0.15 coulombs to the patient. Operator 150 may choose this value because it has been observed to produce good results in a number of typical defibrillation applications. In this case, model waveform determiner 210 determines the additional values of waveform parameters 262 (i.e., the patient impedance and the waveform shape as well as amplitude and duration) needed to achieve the delivery of the desired electric charge to the patient. Determiner 210 makes these determinations using one or more of the other sources of information noted above: waveform data and templates 212, initial impedance sensor 135, and/or operational impedance sensor 130.

For instance, under the control of software, firmware, and/or hardware in accordance with known techniques, determiner 210 activates initial impedance sensor 135. Sensor 135, in a known manner, provides initial patient impedance value 254, which is illustratively assumed to be represented by 50 ohms. Also, determiner 210 selects one of many possible waveform forms, such as biphasic rectilinear. These various forms may conveniently be stored in waveform templates of data and templates 212, and may be retrieved by determiner 210 in accordance with techniques well known to those skilled in the relevant art. This selection may be made based on a predetermined order of preferred waveform forms. For example, research and/or experience may show that a biphasic rectilinear waveform is generally the most effective form for values of desired change within a certain range or within ranges of pulse duration and/or amplitude specified by operator 150. Research and/or experience may show that another waveform form is more effective and/or safe if operator 150 has specified other factors, such as a different desired charge, or if initial patient impedance value 254 is such that excessive currents may be applied using a particular form, and so on.

Having determined the waveform form parameter (i.e., biphasic rectilinear, etc.), determiner 210 determines amplitude(s) and duration(s) parameters such that the desired electric charge is delivered to the patient. For example, it is now illustratively assumed the predetermined form is a monophasic rectilinear pulse of 10 milliseconds duration. It is also assumed for purposes of illustration that the pulse is a voltage pulse, although it may be otherwise. For example, the pulse could be a current pulse. As noted, it is also assumed for initial illustration that initial patient impedance value 254 is represented by an electrical resistance of 50 ohms.

In one implementation, determiner 210 determines the amplitude of this illustrative voltage pulse by applying the relationship that charge is equal to the integral of instantaneous current (voltage divided by resistance in this example) over time. Thus, in this example, determiner 210 determines that a desired charge of 0.15 coulombs is achieved by a rectilinear voltage pulse having a constant amplitude of 750 volts for 10 milliseconds (0.15 coulombs=(750 volts/50 ohms)×10 milliseconds). This determination is made in accordance with known calculation techniques implemented by determiner 210 under the control of programs implemented using software, firmware, hardware, or any combination thereof. Similarly, if operator-selected values 252 had included the requirement that the voltage amplitude must be 750 volts, then determiner 210 would calculate the duration of the pulse to be 10 milliseconds in order to achieve the desired delivery of 0.15 coulombs. If, as another example, initial patient impedance value 254 had been represented by an electrical resistance of 100 ohms, then, as is evident, determiner 210 determines that the amplitude of the voltage pulse is 1500 volts for a duration of 10 milliseconds. In other implementations, determiner 210 may make these and other determinations of intended waveform parameters 264 by using look-up tables, search and compare techniques, or other known techniques. For example, a data table (not shown) in waveform data and templates 212 may provide options for pulse amplitude and duration of various forms, indexed by a desired charge. Thus, using the index variable of 0.15 coulombs, determiner 210 may extract from the table the duration value of 10 milliseconds for a patient impedance value of 100 ohms for a rectilinear voltage pulse of 1500 volts.

As will now be evident to those skilled in the relevant art, determiner 210 may operate in a similar manner upon numerous combinations of operator-selected and/or predetermined values of desired electrical charge to be delivered, patient impedance, forms of waveforms, durations, amplitudes, and other parameters. That is, determiner 210 determines one or more of these values given others using the general relationship that charge equals current over time, and other well known electrical relationships such as that current equals applied voltage divided by the patient impedance.

Determiner 210 may also access data in data and templates 212 that represent various factors related to the amplitude, duration, or other aspects of the shape of the model defibrillation waveform. For example, it may be determined by research or experience that high currents, excessive instantaneous or total energy, and/or other factors reduce defibrillation success by damaging the heart tissue. As additional examples, a pulse having an excessive duration may reduce the chance of successful defibrillation. These factors may be stored in data and templates 212 as predetermined data, and/or they may be entered or adjusted by operator 150 in accordance with known techniques for data representation, storage, and retrieval. If, for example, it is desired to deliver 0.2 coulombs to a patient having an impedance represented by 100 ohms using a rectilinear pulse having a duration of 10 milliseconds, a pulse amplitude of 2000 volts (current of 20 amps) may be determined by determiner 210. However, using any of a variety of known techniques such as search and compare techniques, determiner 210 may consult data and templates 212 to determine that 20 amps is an excessive current to be used in a rectilinear pulse. Therefore, under the control of software, firmware, and/or hardware in accordance with known programming techniques, determiner 210 may extend the duration of the pulse to 20 milliseconds and reduce the voltage amplitude to 1000 volts, thereby achieving the same desired quantity of charge using different waveform parameters. If, however, upon similar consultation of data and templates 212, determiner 210 determines that a duration of 20 milliseconds is excessive, determiner may select another waveform shape and/or provide an indication to operator 150 that the selected desired quantity of charge is not safely achievable.

Similarly, determiner 210 may determine and/or adjust various parameters of intended waveform parameters 264 based on information provided by initial impedance sensor 135 and/or operational impedance sensor 130. As noted, using known techniques, initial impedance sensor 135 senses initial patient impedance value 254 that is indicative of a patient's impedance prior to administering a defibrillation waveform. For example, determiner 210 may, upon being activated by activator 170, send a control signal to sensor 135 instructing it to discharge a small current into the patient for sensing the patient's initial impedance. Also, operational impedance sensor 130 may measure operational patient impedance values 256 by measuring various operational parameters of applied waveform generator 120, such as instantaneous, peak, average, or other measures of currents, voltages, or other values. Using known techniques, these measurements provide indications of the patient's impedance as applied defibrillation waveform 122 is initially being applied (i.e., substantially contemporaneous with the application of the waveform) and/or during part or all of the period of application of the waveform.

As noted, the patient's impedance may change between an initial predetermined or operator-selected value and the value sensed by initial impedance sensor 135, between the value sensed by initial impedance sensor 135 and a value sensed by operational impedance sensor 130, and/or between various values sensed by operational impedance sensor 130 during application of applied defibrillation waveform 122. Determiner 210 adjusts intended waveform parameters 264 in order to maintain the desired quantity of delivered charge in view of the new information regarding patient impedance. For example, if the patient's impedance is sensed to have changed from an initial value represented by a resistance of 50 ohms to a value represented by 100 ohms half way through the 10 millisecond pulse, then determiner 210 may adjust the voltage amplitude from 750 volts to 1500 volts when the patient impedance change is detected. In this manner, the desired delivery of 0.15 coulombs of charge is maintained.

Based on intended waveform parameters 264, controller 215 provides waveform control signals 112 to applied waveform generator 120 so that generator 120 may generate applied defibrillation waveform 122. As noted, the functions of controller 215 could be described as being included in determiner 210, but are separated in this description for purposes of clarity.

Feedback processor 140 applies known techniques to provide controller 215 with feedback regarding whether applied defibrillation waveform 122 conforms to intended waveform parameters 112. More specifically, controller 215 compares indicators of one or more of intended waveform parameters 112 to indicators of system performance (shown as system-performance parameters 262) provided by feedback processor 140. For example, controller 215 may compare a voltage value of intended waveform parameters 112 to an indicator of a corresponding voltage value of applied defibrillation waveform 122 as provided by feedback processor 140. There may be a difference between these amplitudes; i.e., there may be a difference between a waveform-reference parameter and a corresponding system-performance parameter. This difference is referred to for convenience as an error value. In some implementations, if there is an error value, controller 215 brings the actual value into conformance with the desired value by changing waveform control signals 112 to applied waveform generator 120. For example, with reference to an illustrated embodiment described below, controller 215 may adjust waveform control signals 112 to the step-up or step-down converters of generator 120. It may be required that the error value exceed a threshold value before corrective action is taken. Controller 215 thus monitors the error value, and takes corrective action, until the error value is reduced to an acceptable level.

Applied Waveform Generator 120

Figure 3:
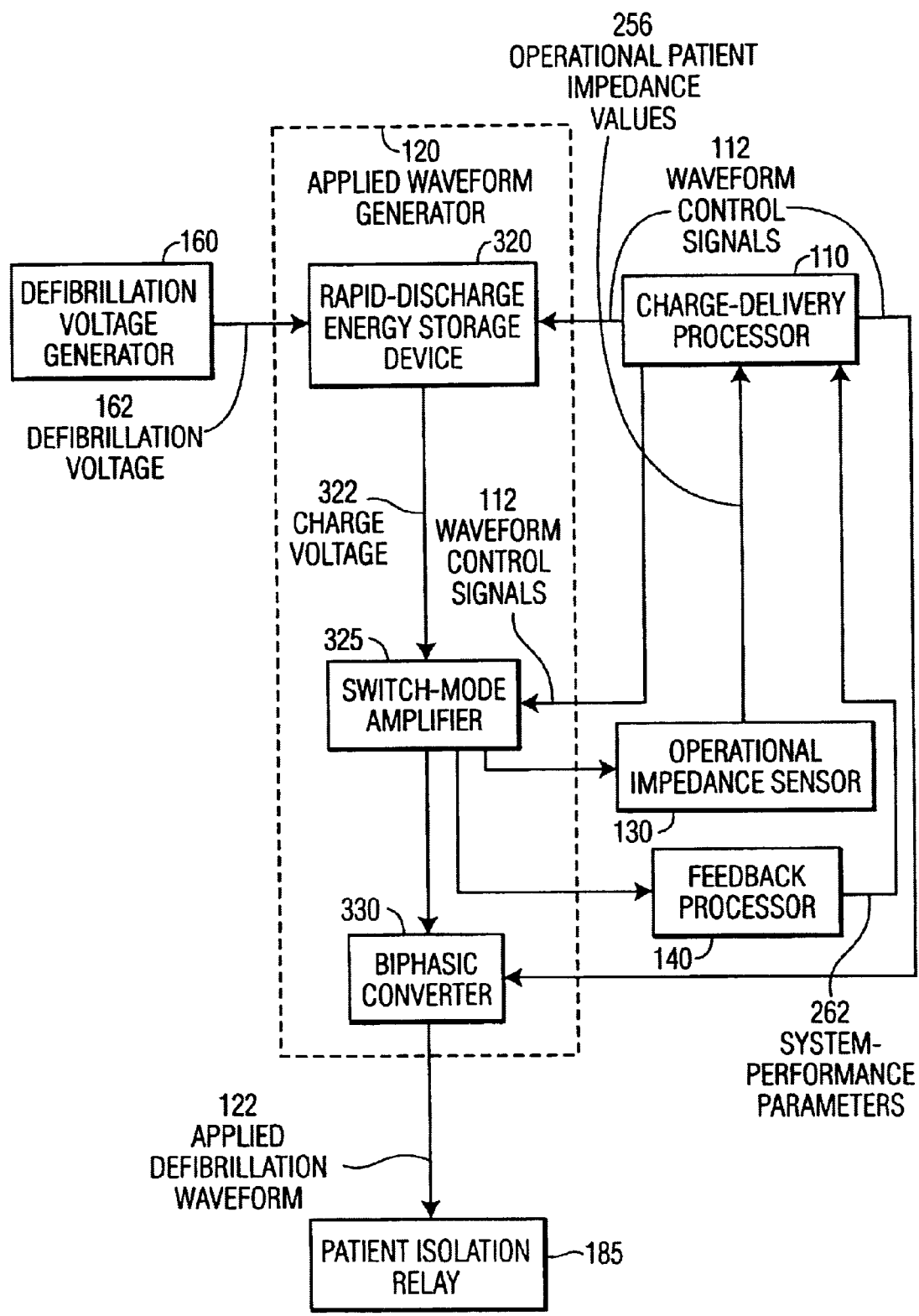
FIG. 3 is a functional block diagram of one embodiment of an applied waveform generator of the charge-determined waveform generator of FIG. 1.

FIG. 3 is a functional block diagram of applied waveform generator 120 that, as noted, generates applied defibrillation waveform 122 based on intended waveform parameters 264. Generator 120 may be any of a variety of devices for generating variable defibrillation waveforms. The word "variable" is used in this context to mean that the waveforms may be adjusted by changing one or more of their amplitude, duration, or form. This capacity for adjustment need not be required if the desired quantity of charge, patient impedance, and other parameters discussed above are predetermined and not adjustable. In that special case, generator 120 need only be capable of generating a predetermined applied defibrillation waveform 122, and the functions of charge-delivery processor 110 may be limited to merely providing data that describes this predetermined waveform. More generally, however, it is advantageous that generator 120 be capable of generating a variable waveform so that applied defibrillation waveform 122 may reflect changes in intended waveform parameters 264 (due, for example, to various selections by operator 150 of desired quantities of charge to be delivered to the patient). For example, the illustration is again assumed in which it is desired to deliver 0.15 coulombs to a patient having an impedance represented by a resistance of 50 ohms, using a rectilinear voltage pulse of amplitude 750 volts and duration of 10 milliseconds. In this case, the applied waveform generator 120 should be capable of generating a pulse of this amplitude and duration in response to waveform control signals 112 from controller 215. Also, applied waveform generator 120 should be capable of generating a pulse of 1000 volts and 10 milliseconds if operator 150 determines that it is desirable to deliver 0.2 coulombs to the patient.

For purposes of convenience and illustration only, it is hereafter assumed that applied waveform generator 120 includes a switch-mode amplifier as described in U.S. patent application Ser. No. 09/191,662, entitled "Method and Apparatus for Providing Variable Defibrillation Waveforms Using Switch-Mode Amplification," naming as inventor Daniel F. Mulhauser, assigned to Hewlett-Packard Company, and filed on Nov. 13, 1998 (hereafter referred to as the Mulhauser application). The disclosure of the Mulhauser application is hereby incorporated herein by reference in its entirety. It will be understood, however, that the present invention is not limited to this illustrated embodiment of applied waveform generator 120.

As shown in FIG. 3, generator 120 includes rapid-discharge energy storage device 320, switch-mode amplifier 325, and biphasic converter 330. Rapid-discharge energy storage device 320 stores energy provided to it from defibrillation voltage generator 160 to build up a charge voltage 322. Typically, in the illustrated embodiment of an external defibrillator, device 320 is any of a variety of known energy storage devices for use in a defibrillator, such as a film capacitor having a capacitance in the range of approximately 30 to 200 microfarads and capable of holding a charge voltage on the order of thousands of volts. In one of many other illustrative examples of known defibrillator rapid-discharge energy storage devices, device 320 may include a number of aluminum electrolytic photo flash capacitors arranged in series. It is not material to the present invention which of many known devices, or others to be developed in the future, are used, provided that device 320 is capable of storing, and rapidly discharging, a charge appropriate for defibrillation.

Figure 4:
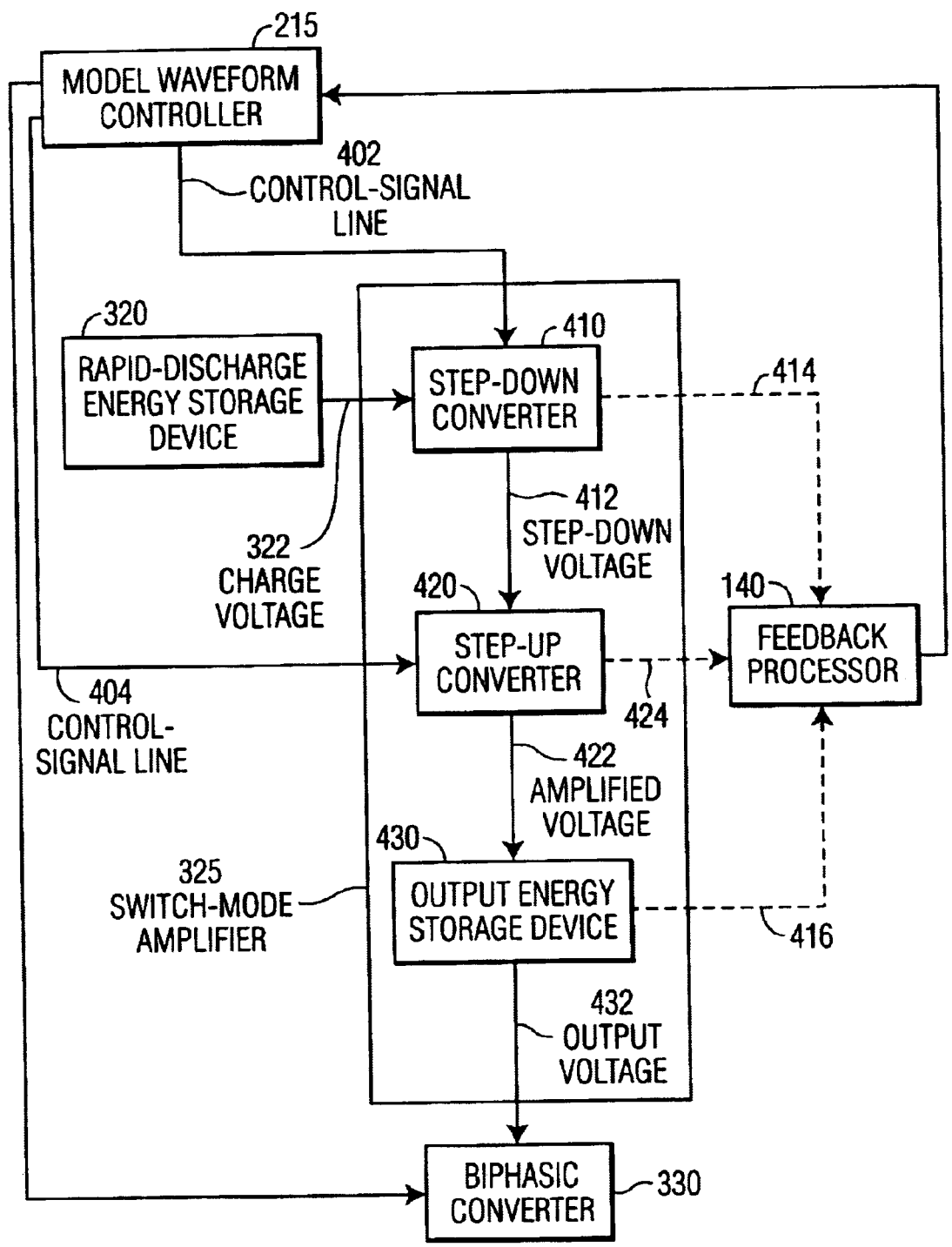
FIG. 4 is a functional block diagram of one embodiment of a switch-mode amplifier of the applied waveform generator of FIG. 3.

FIG. 4 is a functional block diagram of one embodiment of switch-mode amplifier 325. Switch-mode amplifier 325 is illustrative only; many alternative embodiments are possible and it is not material to the present invention which embodiment is used. Amplifier 325 includes step-up converter 420, step-down converter 410, and output energy storage device 430. Alternative implementations of amplifier 325 need not include step-down converter 420 and/or output energy storage device 430. The function of step-up converter 420 (or another type of amplifier in alternative embodiments) to selectively amplify charge voltage 322. In some embodiments, one or both of step-up converter 420 or step-down converter 410 includes an output energy storage device such as device 430. Thus, with respect to references hereafter to step-up converter 420 or step-down converter 410, it will be understood that they may include one or more output energy storage devices, which may be a shared device. For clarity and for illustrative purposes, separate references are also made hereafter to output energy storage device 430.

Step-down converter 410 selectively decreases charge voltage 322 to generate step-down voltage 412. This selective decreasing is accomplished in response to a control signal from controller 215 transmitted over control-signal line 402. Step-up converter 420 receives step-down voltage 412 and selectively amplifies it to generate amplified voltage 422. This selective amplification is accomplished in response to a control signal from controller 215 over control-signal line 404. Output energy storage device 430 receives amplified voltage 422 and filters it to provide output voltage 432, which is provided to biphasic converter 330. Control-signal line 402 and 404 provide aspects of waveform control signals 112 of FIGS. 1 and 2.

Figure 5:
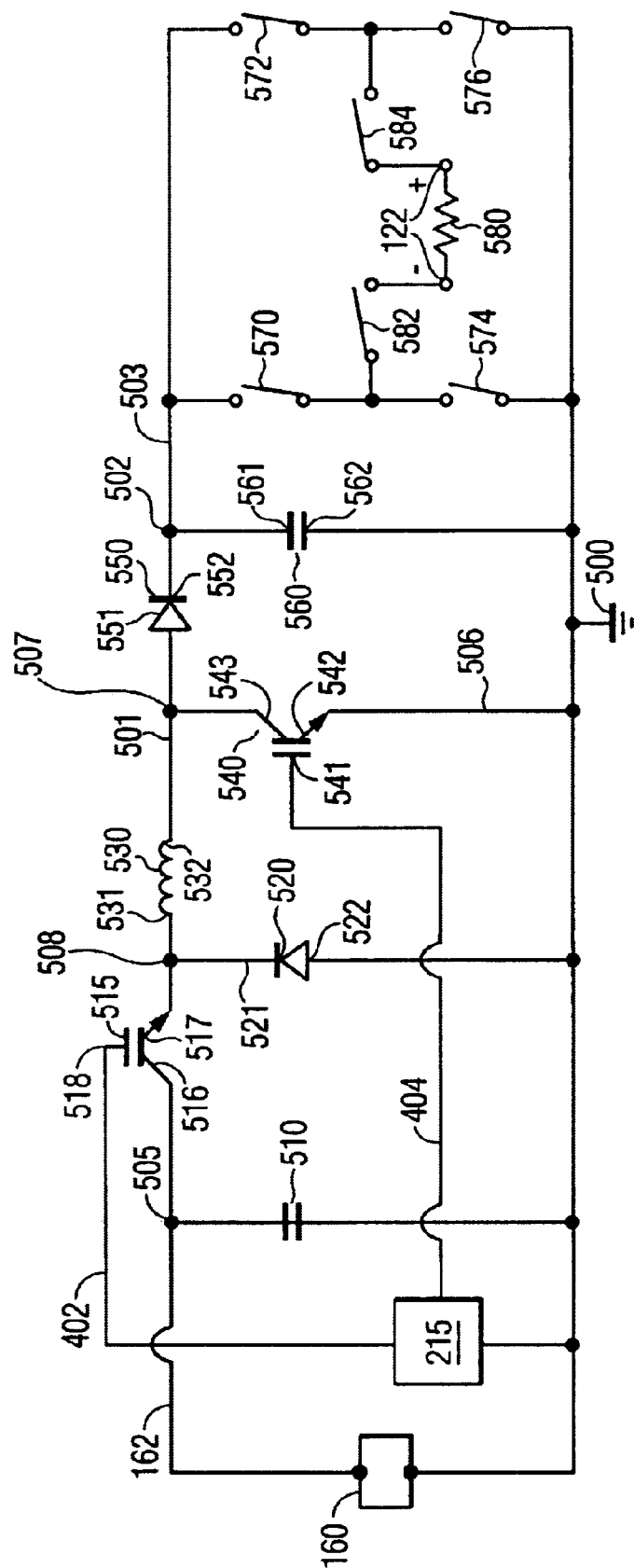
FIG. 5 is a simplified circuit diagram of one implementation of the switch-mode amplifier of FIG. 4, including a biphasic converter of the applied waveform generator of FIG. 3 and a patient isolation relay of the charge-determined waveform generator of FIG. 1.

The operations of switch-mode amplifier 325 are now more fully explained with reference to the simplified circuit diagram of FIG. 5 and the waveforms shown in FIG. 6. FIG. 5 is a circuit diagram of one implementation of the switch-mode amplifier of FIG. 4, including biphasic converter 330 and patient isolation relay 185. It will be understood that the illustrative circuit of FIG. 5 is simplified to depict the principal topology only. It may omit elements or connections where such omissions will be apparent to those skilled in the relevant art. For example, control signals to transistor switches are not shown; rather, for clarity, a simple switch symbol is used to represent transistor switch elements.

The correspondences between the functional elements of FIG. 4 and the circuit elements of FIG. 5 are as follows. Rapid-discharge energy storage device 320 is implemented in the circuit of FIG. 5 by capacitor 510. Output energy storage device 430 is implemented by output capacitor 560. Step-down converter 410 is implemented by buck transistor (hereafter, buck switch) 515, buck diode 520, inductor 530, and capacitor 560. Step-up converter 420 is implemented by boost transistor (hereafter, boost switch) 540, boost diode 550, inductor 530, and capacitor 560. Thus, inductor 530 and capacitor 560 are shared by step-down converter 410 and step-up converter 420 in this implementation, thereby advantageously reducing the number of components required to implement switch-mode amplifier 325. Biphasic converter 330 is implemented by the H-bridge made up of switches 570, 572, 574, and 576. Load resistor 580 represents the impedance of the patient. It will be understood that this representation is a simplification for purposes of illustration, and that patient impedance may also include capacitive and/or inductive components or, more generally, complex resistive and reactive attributes. Patient isolation relay 185 is implemented by switches 582 and 584 (which may be any of a variety of electrical or mechanical switches).

As shown in FIG. 5, defibrillation voltage generator 160 provides defibrillation voltage 162 to one side of capacitor 510 at source node 505. The other side of capacitor 510 is connected to a common voltage 500. For convenience, common voltage 500 is assumed to be ground, but it need not be so. Buck switch 515 has a first node 516 that is connected to source node 505, and a control node 518 that is connected to control-signal line 402 from controller 215. Buck switch 515 also has a second node that is connected to input node 531 of inductor 530, and is also connected to output node 521 of buck diode 520. Buck diode 520 has an input node 522 that is connected to common voltage 500. Inductor 530 has an output node 532 that is connected to a first node 543 of boost switch 540 and to input node 551 of boost diode 550. Boost switch 540 also has a second node 542 that is connected to common voltage 500 and a control node 541 that is connected to controller 215 via control-signal line 404. Boost diode 550 has an output node 552 that is connected to an first node 561 of capacitor 560 and to two legs of the H-bridge consisting of switches 570 and 572.

Capacitor 560 has a common node 562 connected to common voltage 500. The other two legs of the H-bridge consists of switches 574 and 576. As is evident, when switches 570 and 576 on opposite legs of the H-bridge are closed, and switches 572 and 574 are open, and assuming that patient isolation relay switches 582 and 584 are closed, current flows through switch 570, load resistor 580, and switch 576 to common (i.e., to the node connected to common voltage 500). Under the same assumption, when switches 572 and 574 on opposite legs of the H-bridge are closed, and switches 570 and 576 are open, current flows through switch 572, load resistor 580, and switch 574 to common.

As noted, buck switch 515 or boost switch 540 may be implemented by insulated-gate bipolar transistors, field-effect transistors, or other known solid state devices or similar devices now developed or to be developed in the future. Buck diode 520 or boost diode 550 may be implemented by properly synchronized transistor switches. H-bridge switches 570, 572, 574, or 576 may similarly be implemented by insulated-gate bipolar transistors, field-effect transistors, silicon controlled rectifiers, or other known solid state devices or similar devices to be developed in the future. Any of these switches or diodes need not be limited to single components but may include, for example, series or parallel combinations of insulated-gate bipolar transistors, or diodes properly snubbed and controlled for sharing voltage and current. The design and use of such combinations are well known by those skilled in the relevant art.

Figure 6:
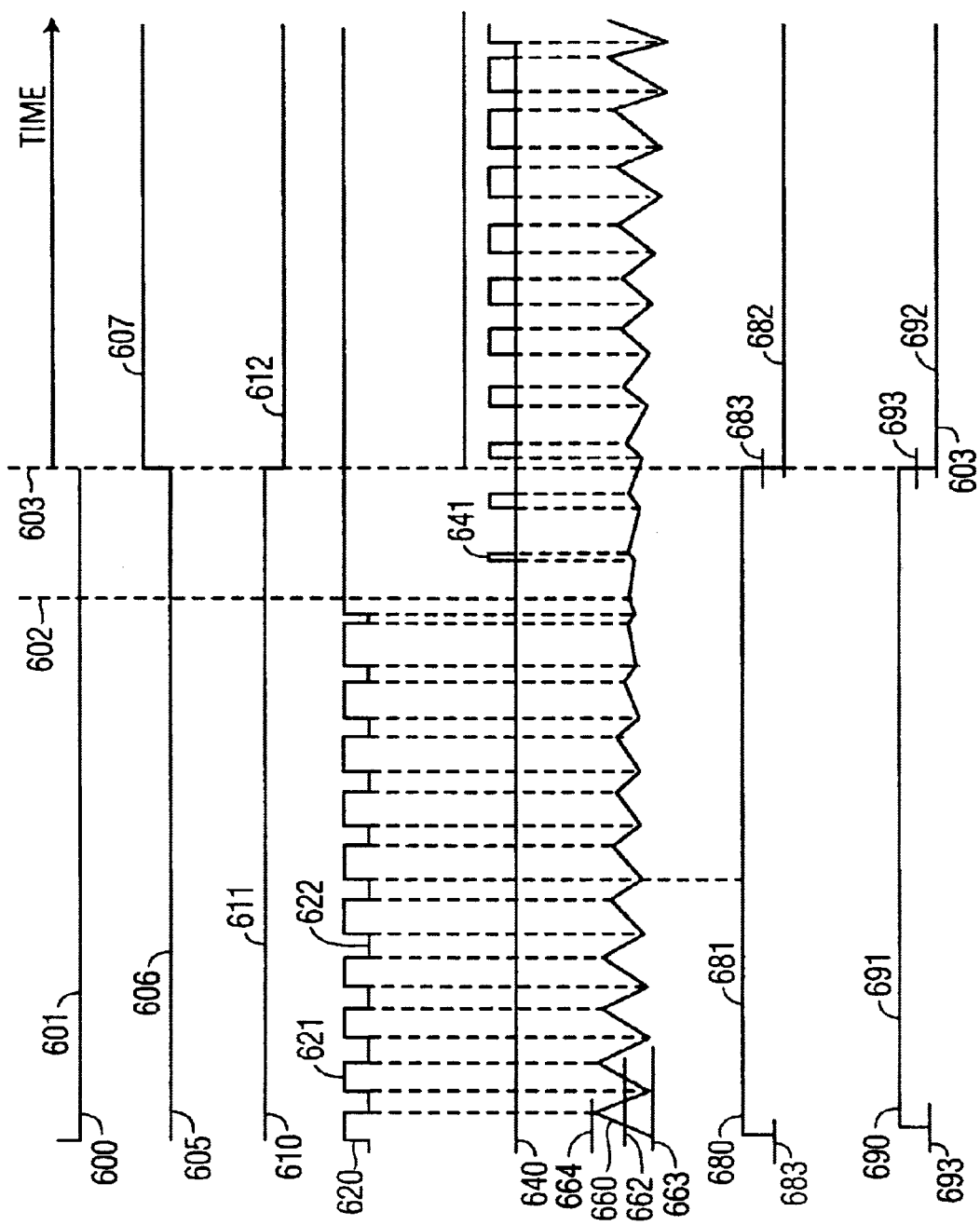
FIG. 6 is a graphical representation of illustrative embodiments of control signals to, and resulting current and voltage waveforms of, selected circuit elements of the circuit of FIG. 5, aligned along a common time axis.

FIG. 6 is a graphical representation of illustrative embodiments of control signals to, and resulting current and voltage waveforms of, selected circuit elements of the circuit of FIG. 5, aligned along a common time axis. This common time axis is represented by time line 600. It is illustratively assumed that, prior to initial time 601 shown on time line 600, operator 150 has activated activator 170 so that defibrillation voltage generator 160 has charged rapid-discharge energy storage device 320 to produce charge voltage 322. It is also illustratively assumed that, prior to initial time 601 and again in response to the activation of activator 170 by operator 150, activator 170 has enabled initial impedance sensor 180.

Control signal 605 controls the states of H-bridge switches 570 and 576. In the illustrative example, control signal 605 is a voltage waveform indicating that, from initial time 601 to a subsequent time 603, a control voltage applied to switches 570 and 576 is in a low state that is arbitrarily assumed for illustrative purposes to indicate that these switches are open. For example, voltage level 606 may be zero volts. At time 603, the voltage level of control signal 605 increases to a positive voltage 607; e.g., five volts. This high voltage state is assumed to indicate that switches 570 and 576 are closed. It will be understood that these voltage levels are arbitrarily chosen in this example, that signals consisting of other than bi-level voltages may be used, and that, more generally, a wide variety of control signals could be used to open and close the switches. In one illustrative implementation consistent with the chronaxie time of the human heart, time 603 may be approximately six milliseconds. As will be evident to those skilled in the relevant art, biphasic conversion is accomplished by switching H-bridge switches 572 and 574 off at approximately the same time switches 570 and 576 are switched on. Thus, in the illustrative implementation, control signal 610 indicates that the switches 572 and 574 are initially closed, as indicated by the initial high voltage 611 (e.g., five volts). At time 603, these switches are opened, as indicated by low voltage 612.

Control signals 605 and 610 are generated in the illustrated embodiment by controller 215 and thus are aspects of waveform control signals 112. Any of a variety of known timing circuits, devices, or techniques may be used to generate these signals. Also, in alternative embodiments, the biphasic control signals for the H-bridge or other biphasic converter need not be generated by controller 215. Rather, they may be provided by timing circuits or devices included in biphasic converter 330 or another element of defibrillator 105. Further, control signals 605 and 610 need not be based on a timing element, but may be triggered by other events such as a voltage at any of the elements of amplifier 325 reaching or crossing predetermined levels.

A flow of current through switches 572 and 574 during the time period between time 601 and time 603 generates what will arbitrarily be termed a "positive" voltage across load resistor 580, as indicated in FIG. 5. Thus, applied defibrillation waveform 122 (the voltage waveform in this example that is applied through the paddles to the patient) has a positive phase during this time period. As is evident, applied defibrillation waveform 122 has a negative phase subsequent to time 603 because current flows in the opposite direction through load resistor 580.

Buck control signal 620 of the illustrated embodiment is a voltage applied to control node 518 of buck switch 515 by controller 215 over control-signal line 402. In the illustrated embodiment, buck switch 515 (like boost switch 540) acts as a switch. It is illustratively assumed that when control signal 620 is in a high state, such as voltage 621 of FIG. 6 (for example, five volts), buck switch 515 is closed. When buck control signal 620 is in a low state, such as voltage 622, buck switch 515 is open. The resulting pulse-width modulation represented by buck control signal 620 (and boost control signal 640 discussed below) are shown in FIG. 6 as being of fixed frequency. However, as will be evident to those skilled in the relevant art, alternative techniques may be used, such as constant on or off time and variable frequency modulation, or hysteretic control.

The time period between initial time 601 and subsequent time 602, as shown on time line 600 of FIG. 6, is a period in which buck switch 515 is intermittently open and closed in accordance with the pulses of buck control signal 620. However, as indicated by the portion of boost control signal 640 from time 601 to time 602, boost switch 540 is constantly open. Thus, this time period may be referred to as the "buck phase." The duration of the buck phase in this illustrative example arbitrarily is assumed to be approximately 4.8 milliseconds. During each on-pulse of buck control signal 620, a current flows through inductor 530 to output capacitor 560, as will be evident to those skilled in the relevant art. That current is represented in FIG. 6 as inductor current waveform 660. In this illustrative example, inductor current waveform 660 varies from a low represented by current level 663, to a high represented by current level 664. An intermediate current level 662 also is shown. Typical values for these current levels in the illustrated embodiment may be 18 amps for current level 663, 20 amps for current level 662, and 22 amps for current level 664. For clarity, these current levels are not drawn across the entire length of the time axis, but are merely suggested at the beginning of the axis. As is evident, the current through inductor 530 increases while buck switch 515 is closed and decreases while buck switch 515 is open and diode 520 is conducting, producing a triangular waveform.

Controller 215 adjusts the widths of the pulses of control signal 620 (or other parameters in alternative implementations of pulse-width or frequency modulation or hysteretic control) to control the current flowing through inductor 530, switch 572, load resistor 580, and switch 574 to common. As is evident, output capacitor 560 provides filtering of the high frequency pulsatile output. With respect to the time periods noted for control signal 620, for example, and for a typical representational patient resistance of approximately 50 ohms, output capacitor 560 may be a film capacitor with a capacitance of approximately one-half to five microfarads, for example.

In one mode of operation, output capacitor 560 also advantageously minimizes leakage current applied to the patient circuit (the circuit through switches 582 and 584, and load resistor 580) just prior to firing of the defibrillator. In this mode, output capacitor 560 does not charge at the same time as rapid-discharge energy storage device 320 charges. Rather, output capacitor 560 charges when the defibrillator is fired. Thus, leakage from buck transistor 515 typically would not have sufficient time to accumulate a dangerous charge on output capacitor 560; i.e., a charge of sufficient magnitude to cause an arc over the patient isolation relays, or that would present a danger to a patient or operator if the relays erroneously closed.

As noted, controller 215 selectively turns buck switch 515 off and on based in part on the indicator of patient impedance, which may be measured by measuring current flow (or voltage levels) at various places in amplifier 325. For example, a current sensor could be positioned at circuit branch 506 as shown in FIG. 5 to measure the current flowing through boost switch 540. Similarly, a current sensor could be positioned at locations such as point 501 (to measure current flowing through inductor 530), point 503 (to measure the output current), at any switch or diode branch, or at any other circuit branch. Appropriate locations at which to place current, and/or voltage, sensors will be evident to those skilled in the relevant art. Feedback processor 140 of FIGS. 1–4 represents this function of sensing the indicator of patient impedance and providing a measure of it to controller 215. Connecting line 424 of FIG. 4 represents an implementation in which a sensor is positioned in step-up converter 420 (such as at circuit branch 506). Connecting line 414 represents an alternative implementation in which a sensor is positioned in step-down converter 410, and connecting line 416 represents yet another implementation in which a sensor is positioned between output energy storage device 430 and biphasic converter 330 (such as at point 503). Lines 424, 414, and 416 are shown as dotted lines to indicate that, in alternative implementations, any one, or any combination, of them may be employed.

As may be noted from FIG. 6, the amplitudes of successive saw teeth of inductor current waveform 660 decline during the buck phase as rapid-discharge energy storage device 320 discharges. Charge voltage 322 thus declines and approaches the output voltage. During this period, the voltage across load resistor 580 is approximately constant due to the choice of the frequency of control signal 620 as compared to the time constant for the LRC circuit represented by output capacitor 560 (e.g., 1 to 5 microfarads), inductor 530, and load resistor 580 (a patient-dependent value that may be, for example, 50 ohms). As is known to those skilled in the relevant art, the average voltage at node 507 is equal to the duty cycle of buck switch 515 times a time-averaged value of the charge voltage 322 (which declines over time). The duty cycle is the ratio of the time that buck switch 515 is closed to the period of constant-frequency pulse-width modulated signal 620.

Thus, by varying the duty cycle during the buck phase (specifically, by increasing it as charge voltage 322 decreases), the voltage at node 502 may be maintained at an approximately constant level, such as voltage 681. In a typical defibrillator application, voltage 681 may be approximately 1,000 volts, for example. In output voltage waveform 680, voltage 681 is shown in relation to a reference voltage 683 that, in this illustrative example, is assumed to be zero volts. Because of the step-down conversion, voltage 681 may be less than the initial value of charge voltage 322. Also, step-down conversion prior to step-up conversion reduces the range of duty cycle over which either conversion stage must operate.

As charge voltage 322 declines, the amplitudes of the teeth of inductor current waveform 660 successively decline until input voltage 322 and the output voltage of applied defibrillation waveform 122 are equal. Controller 215 then initiates a "boost phase," meaning that boost switch 540 has a non-zero duty cycle. At the same time, buck switch 515 remains fully on. In the illustrative example of FIG. 6, this transition from buck phase to boost phase occurs at time 602, as shown on time line 600. During the boost phase, controller 215 increases the duty cycle of boost switch 540 from zero to increasingly larger values. Specifically, with reference to boost control signal 640 of FIG. 6, boost switch 540 is intermittently turned on beginning, in the illustrative example, with positive pulse 641. As may be noted with reference to buck control signal 620, buck switch 515 is turned on during the boost phase. Thus, only one converter is operational at a time, although it need not be so in alternative implementations.

During the boost phase, the boost circuit operation provides a higher voltage at node 502 than is present at node 508 (corresponding to the input to step-up converter 420). This amplification occurs because energy is stored in inductor 530 when boost switch 540 is closed; i.e., boost switch 540 provides a current path to ground so that a current flows through inductor 530. When boost switch 540 is open, the inductive current is forced to flow through boost diode 550, into output capacitor 560, and thence through the H-bridge and load resistor 580. During this time when boost switch 540 is open, the induced voltage across inductor 530 is more positive at node 532, as measured with respect to node 531. Inductor 530 thus increases the voltage at node 502 beyond the voltage level at node 508 as it maintains current flow. During the boost phase, the voltage across load resistor 580 is proportional to charge voltage 322 times the ratio of one divided by one minus the duty cycle. Thus, controller 215 may selectively maintain, or increase, the voltage across load resistor 580 by altering the duty cycle applied via control-signal lines 402 and 404 to buck switch 515 and boost switch 540, respectively. By cascading the H-bridge to the combination of buck and boost stages, the phase of the voltage across load resistor 580 may be varied. Such a phase switch is shown in FIG. 6 at time 603, resulting in a switch of the voltage across load resistor 580 from a positive level of 681 to an equal in magnitude, but negative, level of 682.

Waveform 690 illustrates the current through load resistor 580. As is evident, the shape of current waveform 690 will be the same as that of voltage waveform 680 because load resistor 580 is illustratively assumed to be a pure resistor. In practice, waveforms 680 and 690 may slightly differ because this illustrative assumption may not be precisely accurate. Assuming a resistance of 50 ohms for load resistor 580, and the voltages across it referred to above, current waveform 690 is maintained at a positive level 691 (20 amps) with respect to reference level 693 (0 amps) until time 603. At time 603 the phase shift occurs, and the current through load resistor 580 is shown by level 692 (negative 20 amps).

Figure 7:
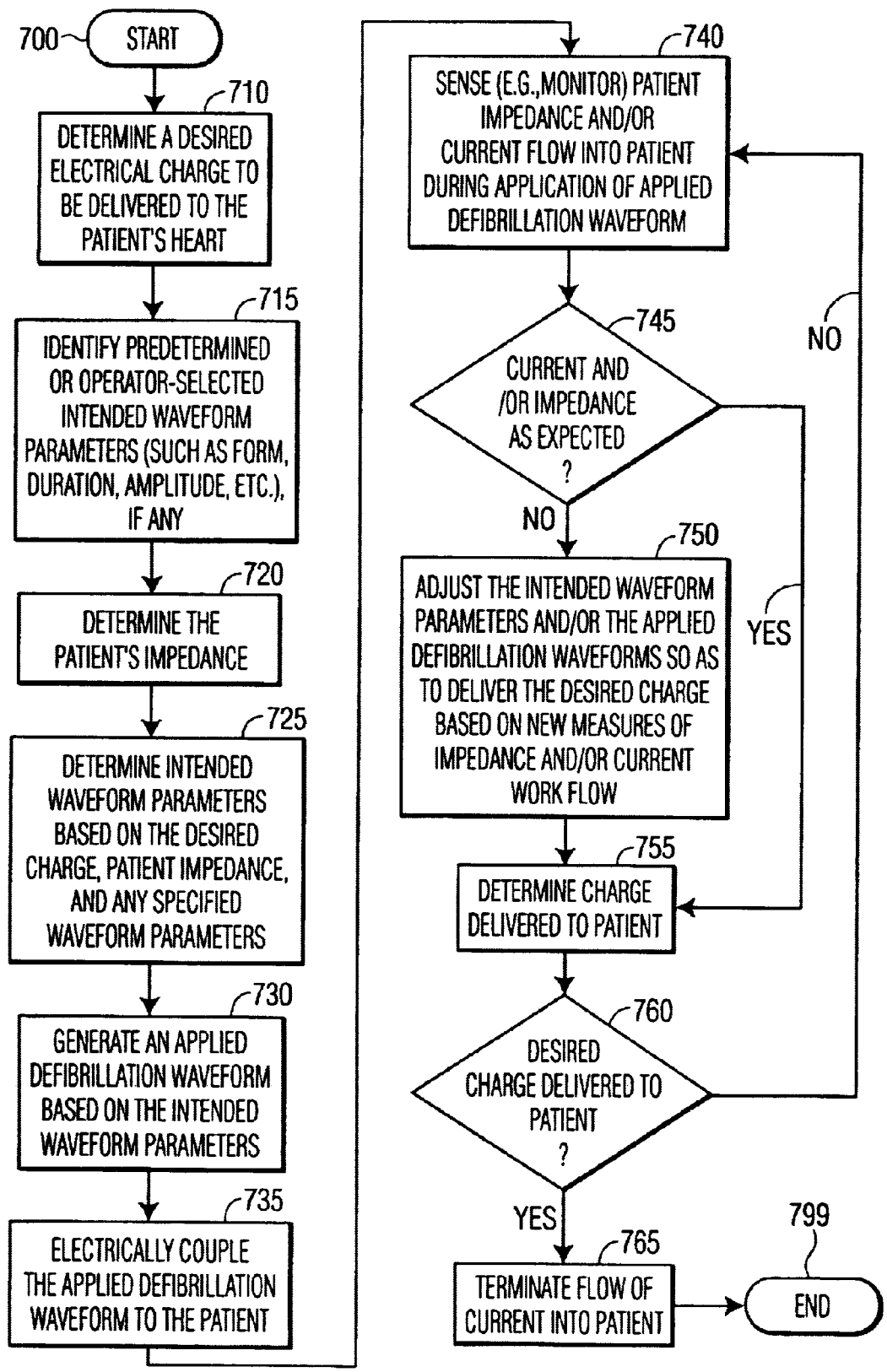
FIG. 7 is a simplified flow chart of one embodiment of a method for delivering a desired quantity of electrical charge to a patient in accordance with the present invention.
Figure 8:
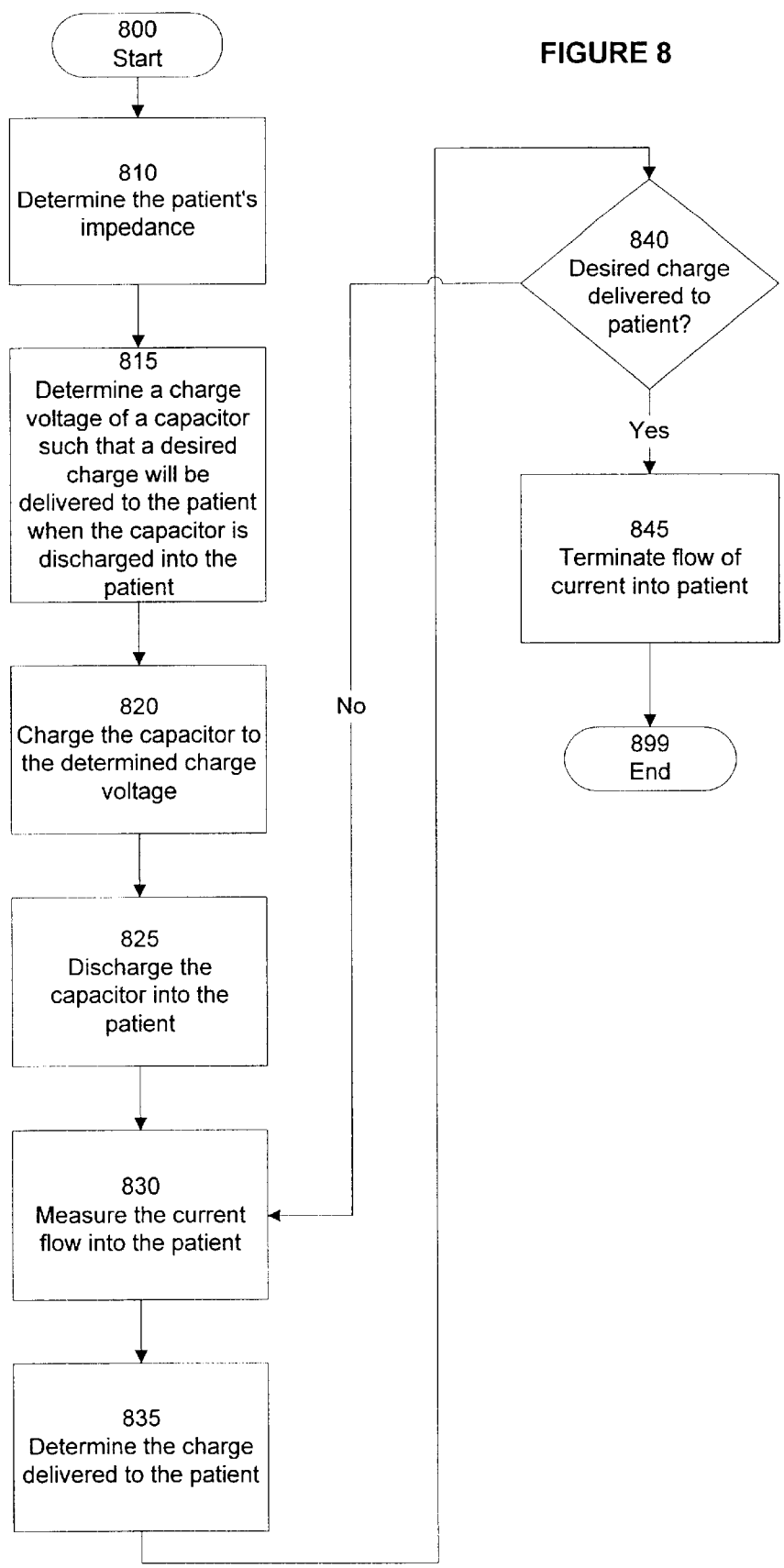
FIG. 8 is a simplified flow chart of another embodiment of a method for delivering a desired quantity of electrical charge to a patient in accordance with the present invention.

FIGS. 7 and 8 are simplified flow charts showing illustrative examples of methods for delivering a desired quantity of electrical charge to a patient in accordance with aspects of the present invention. These methods are now described with reference to functional elements of defibrillator 105 of FIGS. 1 and 2.

With reference to FIG. 7, step 710 is to determine a desired electric charge to be delivered to the patient's heart. As noted with respect to the operations of model waveform determiner 210, the desired electric charge may be predetermined, i.e., a default value stored in waveform data and templates 212 may be used, or it may be selected by operator 150. As represented by step 715, one or more intended waveform parameters may also be predetermined and/or operator-selected. These parameters, if any, are identified. For example, as noted with respect to determiner 210, operator 150 may have selected the form of the waveform to be a rectilinear, monophasic, voltage pulse. As another example, the duration of the waveform may be predetermined to be no longer than 20 milliseconds.

Step 720 is to determine the impedance of the patient. This value or these values may be measured, predetermined, and/or operator-selected. For example, as described above with respect to sensors 130 and 135, they may be measured. As with respect to data stored in waveform data and templates 212, they may be predetermined, or operator-selected values may be stored in waveform data and templates 212 or otherwise processed in accordance with known techniques for acquiring and manipulating user-selected data.

As represented by step 725, a set of intended waveform parameters is determined based on the desired charge as determined in step 710, the patient impedance that was determined in step 720, and any waveform parameters that may have been predetermined and/or operator-selected as noted with respect to step 715. With reference to the illustrated embodiment shown in FIG. 2, this step is undertaken by model waveform determiner 210, thereby generating intended waveform parameters 264. An applied defibrillation waveform (e.g., 122) may be generated by applied waveform generator 120 based on the intended waveform parameters (step 730). This applied defibrillation waveform may (step 735) be applied to the patient.

Additionally, as shown in step 740, sensors (e.g., 130, 135) may be used to sense a value indicative of patient impedance, or sensors or processors (e.g., 140) may be used to measure current flow into the patient during application of the applied defibrillation waveform. If (decision block 745) the current and/or impedance is as expected (e.g., the applied defibrillation waveform is specified by the intended waveform parameters and the amount of charge delivered is as expected), then (step 755) the charge delivered to the patient may be determined. If not, then (750) the intended waveform parameters and/or the applied defibrillation waveform may be adjusted in order to deliver the desired charge based on the new measurements. Charge-determined waveform generator 100 may determine whether the desired charge has been delivered to the patient (decision block 760). If so, then charge-determined waveform generator 100 terminates the flow of current into the patient (step 765). If not, then charge-determined waveform generator 100 continues to monitor the patient impedance and/or current flow as the current continues to flow into the patient (decision block 760 and step 740).

FIG. 8 is a simplified flow diagram showing a method that is directed to another aspect of the invention. The patient's impedance is determined (step 810); for example, it may be user-selected, predetermined, or measured. In this example, this step is done before applying the defibrillation waveform to the patient, but it need not be so in other implementations. In the illustrated method, charge-determined waveform generator 100 determines a charge voltage of a capacitor (which, in other implementations, may be another kind of energy-storage device or voltage/current source) such that a desired (e.g., user-selected or predetermined) charge will be delivered to the patient when the capacitor is discharged into the patient through an appropriate electrical coupling (step 815). The capacitor is charged to this charge voltage (step 820). Then, the charge voltage is discharged from the capacitor to the patient (step 825). In some implementations, as in the illustrated one, the current flow into the patient may be measured (step 830). By computing or otherwise determining the current flowing into the patient over time (step 835), the charge delivered to the patient is determined. If (decision block 840) the desired charge has been delivered, the flow of current into the patient is terminated (step 845). If (decision block 840) the desired charge has not been delivered, the flow of current into the patient continues to be measured and delivered (step 830).

Having now described various aspects of the present invention, it should be apparent to those skilled in the relevant art that the foregoing is illustrative only and not limiting, having been presented by way of example only. For instance, many other schemes for distributing functions among the various functional elements of the illustrated embodiment are possible in accordance with the present invention. The functions of any element may be carried out in various ways in alternative embodiments. Thus, numerous variations are contemplated in accordance with the present invention to generate control signals, detect events or timing information to initiate or end control signals, provide or respond to feedback signals, and so on. There are many possible variations of circuit topologies and circuit elements that may carry out the functions described herein with respect to the present invention.

The functions of determiner 210 and controller 215 may be implemented in accordance with a wide variety of known techniques. For example, they may be implemented by discrete or integrated electronic components, or by a microprocessor. Moreover, the functions described above with respect to determiner 210 and controller 215 may be combined, or some or all of these functions may be distributed among various other functional elements of the invention. For example, control over biphasic converter 330 may be accomplished by a circuit integral with converter 330 rather than provided over a control-signal line from controller 215. Dissipation of stored energy may occur in a separate dump resistor, or in the inductor if properly controlled. The method steps shown in FIGS. 7 and 8 also are illustrative only. Steps and/or decision elements may be combined, separated, carried out in other orders or sequences, carried out in parallel, or otherwise rearranged in alternative embodiments. Also, additional steps and/or decision elements may be added in alternative embodiments. Numerous other embodiments, and modifications thereof, are contemplated as falling within the scope of the present invention as defined by appended claims and equivalents thereto.

What is claimed is:

1. A method for delivering a desired quantity of electric charge to a patient, comprising the steps of:

(1) determining, as one or more intended waveform parameters, at least one of an initial shape and initial amplitude of a waveform based at least in part on a predetermined electric charge table;

(2) generating an applied defibrillation waveform based on the intended waveform parameters;

(3) simultaneously, sensing a value indicative of an impedance of the patient during the execution of step 2;

(4) determining an adjustment, if any, to one or more of the one or more intended waveform parameters based at least in part on the sensed value; and (5) adjusting the applied defibrillation waveform in accordance with step (4).

2. The method of claim 1, wherein:

an operator selectively provides the intended waveform parameters.

3. The method of claim 1, further comprising the step of:

(3) electrically coupling the applied defibrillation waveform to the patient.

4. The method of claim 1, wherein:

the waveform parameters are selected from any one or more of the group consisting of: form, phase, timing of phase transition, maximum duration, minimum duration, maximum voltage, minimum voltage, maximum current, minimum current, maximum energy, minimum energy, maximum power, and minimum power.

5. The method of claim 1, wherein:

the impedance of the patient is predetermined.

6. The method of claim 1, further comprising the steps of:

(3) during execution of step (2), comparing one or more of the one or more intended waveform parameters with the applied defibrillation waveform; and (5) when a difference between the intended waveform parameters and the applied defibrillation waveform reaches a threshold value, adjusting the applied defibrillator waveform to conform with the intended waveform parameters.

7. The method of claim 1, wherein:

the patient impedance is a transthoracic impedance.

8. The method of claim 1, wherein:

the patient impedance is a heart impedance.

9. The method of claim 1, wherein:

the applied defibrillation waveform comprises a monophasic voltage pulse.

10. The method of claim 1, wherein:

the applied defibrillation waveform comprises a biphasic voltage pulse having first and second phases of opposing polarities.

11. A defibrillator for delivering a desired quantity of therapeutic electric charge to a patient, comprising:

a charge-delivery processor constructed and arranged to determine, as one or more intended waveform parameters and based at least in part on a predetermined electric charge table, at least one of an initial shape and initial amplitude of a waveform and to deliver a flow of current over time to the patient;

an applied waveform generator constructed and arranged to apply a defibrillation waveform to the patient based on one or more of the one or more intended waveform parameters; and at least one sensor constructed and arranged to sense one or more values indicative of said flow, wherein the charge-delivery processor further is constructed and arranged to determine an adjustment, if any, to one or more of the one or more intended waveform parameters based at least in part on the sensed one or more values of the sensor.

12. The defibrillator of claim 11, wherein:

a first of the at least one sensor senses a value indicative of an impedance of the patient prior to the charge-delivery processor determining the one or more intended waveform parameters.

13. A method for delivering a desired quantity of electric charge to a patient, comprising the steps of:

(1) determining, as one or more intended waveform parameters, at least one of an initial shape and initial amplitude of a waveform based at least in part on a predetermined electric charge table;

(2) generating an applied defibrillation waveform based on the intended waveform parameters;

(3) simultaneously, sensing one or more values indicative of one or more impedances of the patient during the execution of step (2);

(4) determining an adjustment, if any, to one or more of the one or more intended waveform parameters based at least in part on the sensed value; and (5) adjusting the applied defibrillation waveform in accordance with step (4).

14. The method of claim 13, wherein:

an operator selectively provides the intended waveform parameters.

15. The method of claim 13, wherein:

the patient impedance is a transthoracic impedance.

16. The method of claim 13, wherein:

the patient impedance is a heart impedance.

* * * * *